(12) United States Patent
Feyh et al.

(10) Patent No.: US 10,060,888 B2
(45) Date of Patent: Aug. 28, 2018

(54) MEMS GAS CHROMATOGRAPH AND METHOD OF FORMING A SEPARATOR COLUMN FOR A MEMS GAS CHROMATOGRAPH

(71) Applicants: ROBERT BOSCH GMBH, Stuttgart (DE); Ando Feyh, Reutlingen (DE); Gary O'Brien, Palo Alto, CA (US); Bongsang Kim, Mountain View, CA (US); Jochen Stehle, Palo Alto, CA (US)

(72) Inventors: Ando Feyh, Reutlingen (DE); Gary O'Brien, Palo Alto, CA (US); Bongsang Kim, Mountain View, CA (US); Jochen Stehle, Palo Alto, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/535,522

(22) PCT Filed: Dec. 16, 2015

(86) PCT No.: PCT/US2015/066076
§ 371 (c)(1),
(2) Date: Jun. 13, 2017

(87) PCT Pub. No.: WO2016/100504
PCT Pub. Date: Jun. 23, 2016

(65) Prior Publication Data
US 2017/0363588 A1    Dec. 21, 2017

Related U.S. Application Data

(60) Provisional application No. 62/093,047, filed on Dec. 17, 2014.

(51) Int. Cl.
*G01N 30/60* (2006.01)
*G01N 30/02* (2006.01)
(Continued)

(52) U.S. Cl.
CPC ......... *G01N 30/6095* (2013.01); *B81B 1/002* (2013.01); *B81C 1/00119* (2013.01); *G01N 2030/025* (2013.01)

(58) Field of Classification Search
None
See application file for complete search history.

(56) References Cited

U.S. PATENT DOCUMENTS

| 7,582,514 B2 | 9/2009 | Vancura et al. |
| 2013/0126989 A1 | 5/2013 | Lin et al. |

FOREIGN PATENT DOCUMENTS

WO    2010/136986 A2    12/2010

OTHER PUBLICATIONS

International Search Report corresponding to PCT Application No. PCT/US2015/066076, dated Jun. 28, 2016 (3 pages).
(Continued)

*Primary Examiner* — Whitney T Moore
(74) *Attorney, Agent, or Firm* — Maginot Moore & Beck LLP

(57) ABSTRACT

A micro gas chromatograph includes one or more separator columns formed within a device layer. The separator columns have small channel cross sections and long channel lengths with atomic-smooth channel sidewalls enabling a high channel packaging density, multiple channels positioned on top of each other, and channel segments that are thermally decoupled from the substrates. The micro gas-chromatograph also enables electrostatic and thermal actuators to be positioned in close proximity to the separator columns such that the material passing through the columns
(Continued)

is one or more of locally heated, locally cooled, and electrically biased.

20 Claims, 10 Drawing Sheets

(51) Int. Cl.
*B81C 1/00* (2006.01)
*B81B 1/00* (2006.01)

(56) References Cited

OTHER PUBLICATIONS

Zandi et al.; Design and Demonstration of an In-Plane Silicon-on-Insulator Optical MEMS Fabry-Pérot-Based Accelerometer Integrated With Channel Waveguides; Journal of Microelectromechanical Systems; Dec. 2012; pp. 1464-1470; vol. 21, No. 6.
De Boer et al.; Micromachining of Buried Micro Channels in Silicon; Journal of Microelectromechanical Systems; Mar. 2000; pp. 94-103; vol. 9, No. 1.
Zareian-Jahromi, Mohammad; MEMS-Based Micro Gas Chromatography: Design, Fabrication and Characterization; Thesis, Virginia Polytechnic Institute and State University; May 22, 2009 (71 pages).
Mizushima et al.; Empty-space-in-silicon technique for fabricating a silicon-on-nothing structure; Applied Physics Letters; Nov. 13, 2000; pp. 3290-3292; vol. 77, No. 20.

MEMS GAS CHROMATOGRAPH AND METHOD OF FORMING A SEPARATOR COLUMN FOR A MEMS GAS CHROMATOGRAPH

This application is a 35 U.S.C. § 371 National Stage Application of PCT/US2015/066076, filed on Dec. 16, 2015, which claims the benefit of priority to U.S. Provisional Application No. 62/093,047, filed Dec. 17, 2014, the disclosures of which are incorporated herein by reference in its their entirety.

TECHNICAL FIELD

The disclosure relates to chemical sensors and, more particularly, to micro gas chromatographs.

BACKGROUND

Micro gas chromatography (μGC) systems provide a portable, cost effective alternative to conventional gas chromatography (GC) systems and have a wide range of applications in industries such as pharmaceutical, environmental monitoring, petroleum distillation, clinical chemistry, and food processing. A typical μGC system is a hybrid integration of several micro-scale modules such as a preconcentrator, a separation column, a gas detector, and a plurality of micro valves and pumps. A μGC system benefits from a separator column having a smooth sidewall profile to improve measurement accuracy and function as an effective alternative to conventional GC systems. Such μGC systems also benefit from separator columns formed with small channel cross sections and long channel lengths.

The separator columns of existing μGC systems are often formed by using an etching process to define the column in the substrate or by using a mold. These manufacturing methods make formation of a smooth sidewall profile difficult due to the inherent limitations of these processes. The packaging density of a separator column formed by these existing methods is also limited due the limitations in the scale of the features that can be produced using etching or mold techniques to form the separator column.

What is needed, therefore, is a micro gas chromatograph with atomic smooth channel sidewalls and a high channel packaging density. A manufacturing method that enables production of a micro gas chromatograph with atomic smooth channel sidewalls and a high channel packaging density is further desirable.

SUMMARY

A method of forming a microelectromechanical system (MEMS) device includes providing a silicon-on-insulator (SOI) wafer including a base layer, a device layer above the base layer, and a buried oxide layer between the base layer and a lower surface of the device layer, etching a plurality of trenches from an upper surface of the device layer to the buried oxide layer, the trenches spaced along a sequential path in the device layer, releasing a portion of the buried oxide layer through the trenches, and annealing the SOI wafer to seal off the trenches at the upper and lower surfaces of the device layer so as to form (i) one or more atomic-smooth, continuous channels within the device layer and (ii) a cavity bounded by the base layer, the buried oxide layer, and the lower surface of the device layer.

In embodiments of the method, the one or more atomic-smooth, continuous channels includes a first continuous channel and a second continuous channel, and the device layer defines (i) a first ingress leading into the first continuous channel and a first egress leading out of first continuous channel and (ii) a second ingress leading into the second continuous channel and a second egress leading out of the second continuous channel, the first continuous channel is disposed substantially along a first plane through the device layer, the second continuous channel is disposed substantially along a second plane through the device layer, the second plane spaced from the first plane, and the first egress of the first continuous channel is joined to the second ingress of the second continuous channel such that first and second continuous channels form a single continuous channel passing through the device layer.

In embodiments of the method, the method includes etching a trench portion from the upper surface of the device layer to the buried oxide layer, the trench portion encompassing a first portion of the device layer that includes the one or more atomic-smooth, continuous channels, filling the trench portion with an oxide, depositing a passivation layer above the device layer and the oxide-filled trench portion, etching a plurality of vent holes through the passivation layer at locations corresponding to the oxide-filled trench portion, releasing the oxide from within the trench portion to thermally decouple the first portion of the device layer from a second portion of the device layer, and sealing the vent holes, releasing the oxide from within the trench portion includes performing a hydrofluoric acid (HF) vapor etch release, and sealing the vent holes includes performing a clean high temperature seal in an epi reactor.

In embodiments of the method, the method includes forming a spacer from the upper surface of the device layer to the buried oxide layer to electrically isolate a side electrode within the device layer prior to etching the plurality of trenches, the spacer positioned proximate to at least a portion of the one or more atomic-smooth continuous channels, depositing a passivation layer above the device layer, the spacer and the side electrode, patterning a portion of the passivation layer to expose the side electrode, depositing a metal layer above the patterned passivation layer and the exposed side electrode, and patterning the metal layer to form a metal portion that is in electrical communication with the side electrode, the metal portion and the side electrode enabling electrostatic biasing of a material conveyed through the one or more atomic-smooth, continuous channels.

In embodiments of the method, the method includes depositing a passivation layer above the device layer, depositing a metal layer above the passivation layer, patterning the metal layer to form a metal portion proximate to a portion of the one or more atomic-smooth, continuous channels, the metal portion is configured as one more of an upper electrode, a local heater element, and a Seebeck element, the sequential path of the spaced trenches forms one or more of a repeating square wave, a repeating sine wave, a triangular wave, a sawtooth wave, and a meandering path through the device layer when viewed facing the upper surface of the device layer from above, the sequential path of spaced trenches includes trenches that are arranged in one or more of (i) a single-file line, one-trench-behind-the-other-trench and (ii) two or more trenches wide when viewed facing the upper surface of the device layer from above, the one or more atomic-smooth, continuous channels have cross sections that are one or more of constant, variable, and a combination of constant and variable portions when viewed along a section plane that passes perpendicular to a path of the channels through the device layer.

In embodiments of the method, annealing the SOI wafer comprises annealing the SOI wafer in a reducing ambient, at an elevated temperature greater than 1000 degrees Celsius, and for a duration of 10 seconds to 10 minutes, releasing a portion of the buried oxide layer comprises performing a hydrofluoric acid (HF) vapor etch release, providing an SOI wafer comprises one of providing an SOI wafer having a device layer with a relatively thick layer thickness such that subsequent annealing of the SOI wafer forms at least two atomic-smooth, continuous channels within the device layer, or providing an SOI wafer having a device layer with a relatively thin layer thickness such that subsequent annealing of the SOI wafer forms one atomic-smooth, continuous channel within the device layer.

A microelectromechanical system (MEMS) device includes a base layer, a device layer supported vertically above the base layer by a portion of a buried oxide layer, a cavity within the buried oxide layer and extending horizontally between the base layer and a released portion of the device layer, and a passivation layer supporting the released portion of the device layer above the cavity, the released portion includes at least one channel extending horizontally within the released portion beneath an upper surface of the released portion and a above lower surface of the released portion.

In embodiments of the MEMS device, a side electrode is defined within the released portion of the device layer by a spacer comprising a nitride portion, the side electrode positioned proximate to a portion of the at least one channel, and a metal portion extends through a portion of the passivation layer such that the metal portion is in electrical communication with the side electrode, a trench portion extends between the passivation layer and the cavity, the trench portion encompassing the released portion of the device layer such that the trench portion and the cavity thermally decouple the released portion from an unreleased portion of the device layer, the at least one channel includes a first channel and a second channel, and the released portion of the device layer defines (i) a first ingress leading into the first channel and a first egress leading out of first channel and (ii) a second ingress leading into the second channel and a second egress leading out of the second channel.

In embodiments of the MEMS device, the first channel is disposed substantially along a first plane through the released portion of the device layer, and the second channel is disposed substantially along a second plane through the released portion of the device layer, the second plane spaced from the first plane, the first and second channels are disposed substantially along a common plane through the released portion of the device layer, and the device layer is a layer of either mono- or poly-crystalline silicon having a thickness of approximately 5 to 50 μm, and the buried oxide layer has a thickness of approximately 0.5 to 2.5 μm.

DESCRIPTION

Figure 1:
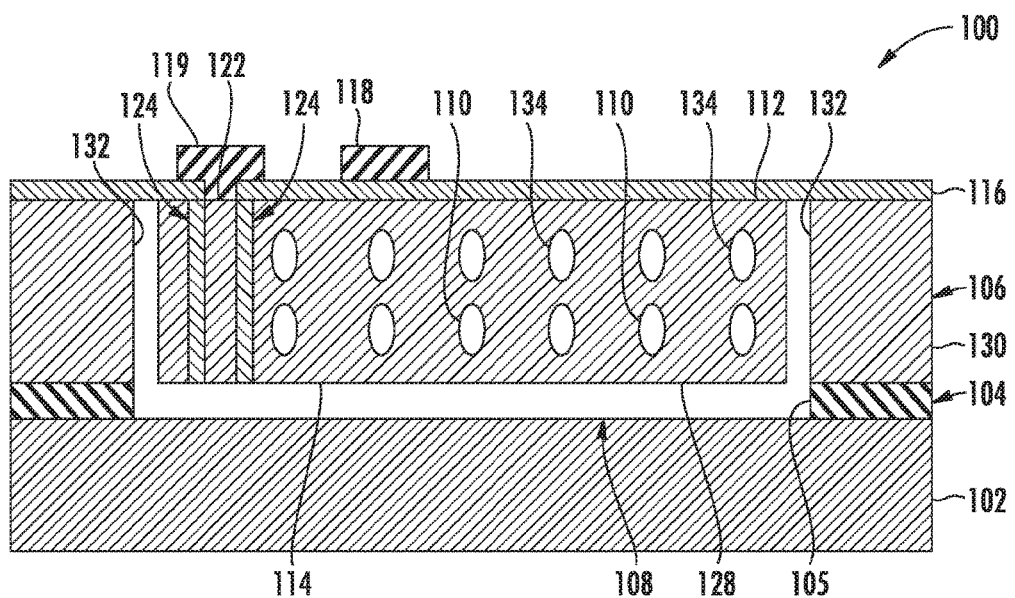
FIG. 1 depicts a side cross-sectional view of a first embodiment of an electronic device with two continuous channels incorporated within a device layer to convey a material therethrough.

For the purpose of promoting an understanding of the principles of the disclosure, reference will now be made to the embodiments illustrated in the drawings and described in the following written specification. It is understood that no limitation to the scope of the disclosure is thereby intended. It is further understood that the disclosure includes any alterations and modifications to the illustrated embodiments and includes further applications of the principles of the disclosure as would normally occur to one skilled in the art to which this disclosure pertains.

Figure 2:
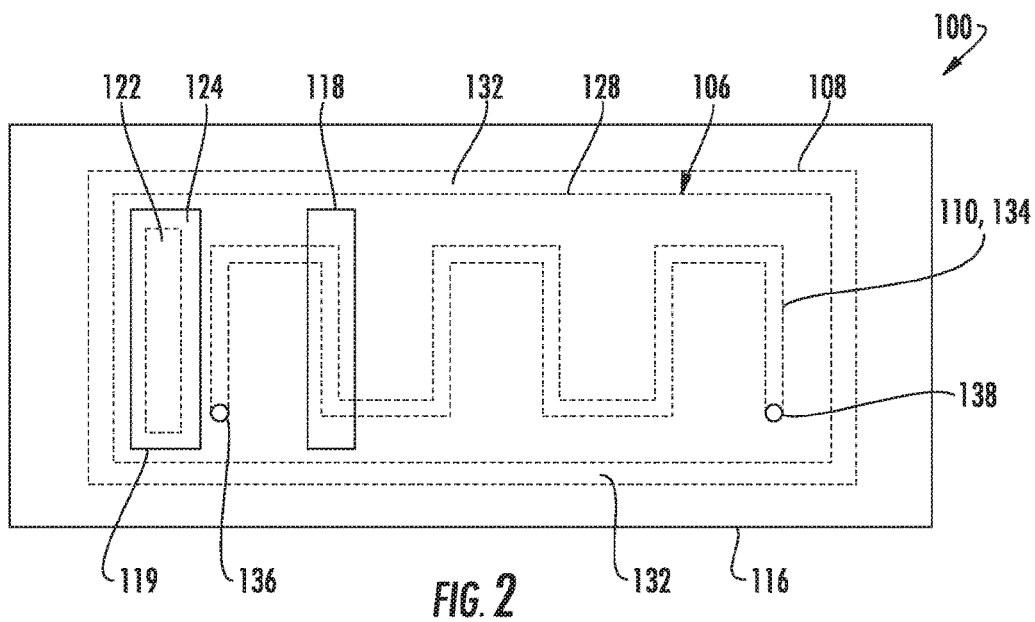
FIG. 2 depicts a top view of the electronic device of FIG. 1 with features of the device encompassed within the device layer shown in hidden lines.

FIGS. 1 and 2 depict a section view and a top view, respectively, of an electronic device 100 according to a first embodiment. The electronic device 100 includes a base layer 102, a buried oxide layer 104, and a device layer 106. The buried oxide layer 104 separates the base layer 102 from the device layer 106. A cavity 108 etched from a portion of the buried oxide layer 104 isolates a portion of the base layer 102 from the device layer 106. The device layer 106 is anchored to the base layer 102 by a portion 105 of the buried oxide layer 104 that remains after the etching of the cavity 108.

Within the device layer 106, a continuous first channel 110 is disposed between an upper surface 112 and a lower surface 114 of the device layer 106. The first channel 110 in the embodiment shown extends substantially along a first plane spaced between the upper and the lower surfaces 112, 114. In other embodiments, the first channel 110 extends in a variable manner along, above, and/or below the first plane such that the first channel 110 forms a first undulating channel enclosed within the device layer 106.

The electronic device 100 also includes a continuous second channel 134 disposed between the upper surface 112 and the first channel 110 within the cap layer 106. The second channel 134 in the embodiment shown extends substantially along a second plane spaced between the upper surface 112 and the first channel 110. In other embodiments, the second channel 134 extends in a variable manner along, above, and/or below the second plane such that the second channel 134 forms an undulating channel enclosed within the device layer 106. In the embodiment shown in FIG. 2, the first channel 110 and the second channel 134 are aligned such that the path of the first channel 110 through the cap layer 106 is shown as identical to the path of the second channel 134 through the cap layer 106. In other embodiments, the path of the first channel 110 includes at least some portions that are different than the path of the second channel 134.

The first channel 110 and the second channel 134 are configured to enable a material, such as a gaseous composition, to pass through the channels 110, 134 between at least one ingress portion and at least one egress portion. In the embodiment shown, the first channel 110 includes a first ingress portion (not shown) that enables the material to enter the first channel 110 and a first egress portion (not shown) that enables material to exit the first channel 210. Similarly, the second channel 134 includes a second ingress portion 136 that allows material to enter the second channel 134 and a second egress portion 138 that enables material to exit the second channel 134. In other embodiments, the first channel 110 and the second channel 134 are joined such that the material enters the channels 110, 134 at the ingress portion of one channel, passes through the channels 110, 134, and exits the channels 110, 134 at the egress portion of the other channel.

Although the ingress portion 136 and the egress portion 138 of the second channel 134 are shown at specific locations in FIG. 2, these portions 136, 138 in other embodiments can be located at different positions in the device layer 106. Similarly, the ingress and the egress portions of the first channel 110 can be located at different positions in the device layer 106. In embodiments with the first channel 110 and the second channel 134 joined, the ingress portion and the egress portion can also be located at positions different than those positions depicted in FIG. 2.

With particular reference to FIG. 1, the first channel 110 is shown having an oval-shaped cross section when viewed along a section plane that passes perpendicular to the path of the channel through the device layer 106. In other embodiments, the first channel 110 has a cross section different than the oval-shaped cross section. The cross section of the first channel in any embodiment can be constant, variable, or can include both constant and variable portions along the channel path. The second channel 134 is also shown having an oval-shaped cross section when viewed along the section plane. In other embodiments, the second channel 134 has a cross section different than the oval-shaped cross section. The cross section of the second channel 134 in any embodiment can be constant, variable, or can include both constant and variable portions along the channel path. In some embodiments, at least some portions of the first channel 110 have cross sections that are different than the cross section of the second channel 134.

Referring again to FIGS. 1 and 2, the electronic device 100 is shown with a passivation layer 116 located above the device layer 106. A first metal portion 118 is disposed above the passivation layer 116 and positioned proximate to at least a portion of the channels 110, 134. In some embodiments, the first metal portion 118 is configured as an upper electrode that electrostatically biases the material that passes through the portion of the channels 110, 134 near the upper electrode. The first metal portion 118 in other embodiments is configured as a local heater element that locally heats the material passing through the channels 110, 134 near the heater element. In yet further embodiments, the first metal portion 118 is configured as a Seebeck element utilizing the Seebeck effect to actively heat or cool the material passing through the channel 110, 134. The passivation layer 116 in any of these embodiments electrically insulates the first metal portion 118 from the device layer 106.

The electronic device 100 further includes a side electrode 122 defined within the device layer 106 by at least one spacer 124. The spacer 124 includes a nitride portion that extends through the device layer 106 and between the cavity 108 and the passivation layer 116 to electrically insulate the side electrode 122 from the device layer 106. The passivation layer 116 includes a contact portion that enables a second metal portion 119 to contact the side electrode 122 for electrical communication therebetween. The side electrode 122 is positioned proximate to at least a portion of the channels 110, 134 such that side electrode 122 can electrostatically bias the material passing through the portion of the channels 110, 134 near the side electrode 122.

A trench portion 132 extends through the device layer 106 and between the passivation layer 116 and the cavity 108 to isolate a first portion 128 of the device layer 106 from a second portion 130 of the device layer. As shown in the figures, the first and the second channels 110, 134 are substantially encompassed within the first portion 128 of the device layer 106. The trench portion 132 and the cavity 108 are configured to thermally decouple the first portion 128 of the device layer 106 from the second portion 130 of the device layer 106. In the embodiment shown, the passivation layer 116 substantially supports the first portion 128 of the device layer 106 and anchors the first portion 128 to the base layer 102 by connection to the second portion 130 of the device layer 106, which in turn is connected to the buried oxide portion 105.

Figure 3:
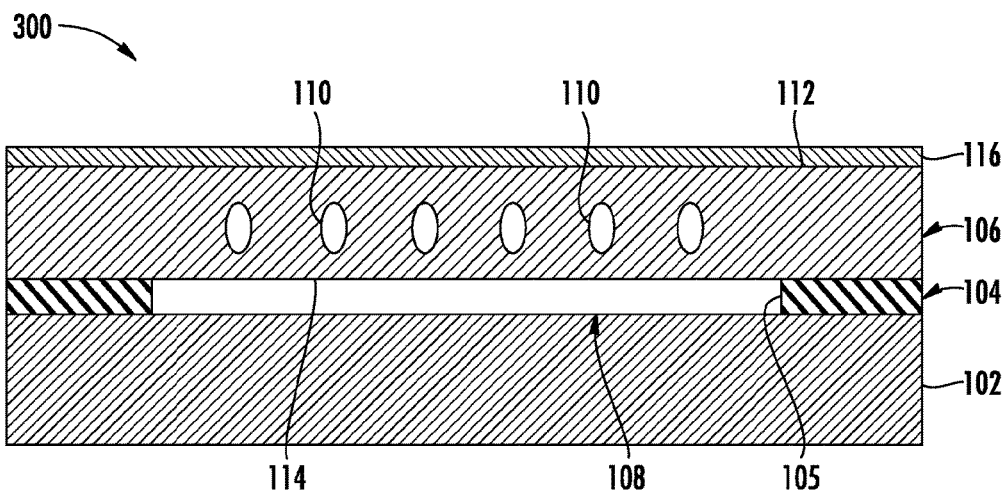
FIG. 3 shows an embodiment of an electronic device with a single continuous channel incorporated within a device layer to convey a material therethrough.
Figure 4:
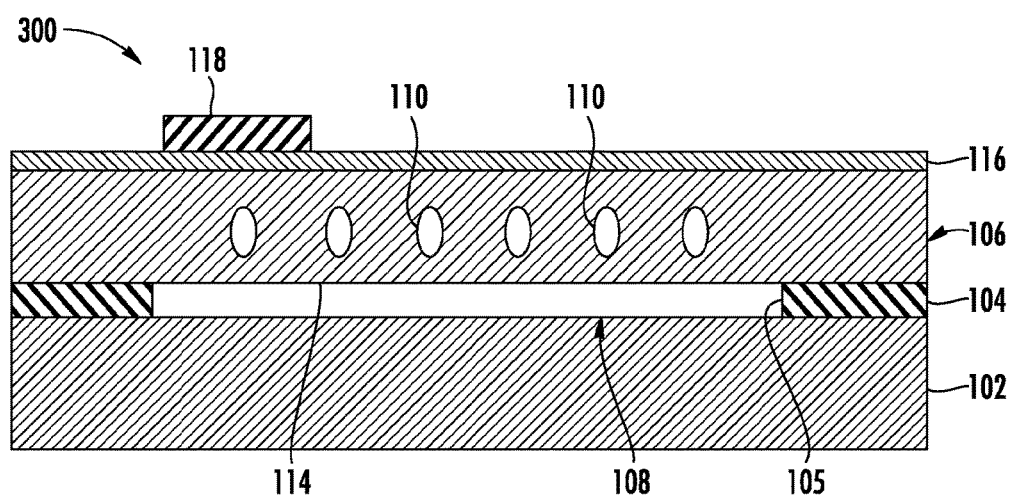
FIG. 4 shows the electronic device of FIG. 3 with a metal portion located proximately above a portion the channel for one or more electrostatically biasing, passively heating, and actively heating or cooling the conveyed material.

FIGS. 3-6 depict alternative embodiments of an electronic device provided by omitting and/or combining selected features of the electronic device 100 of FIG. 1. FIG. 3 shows an electronic device 200 including only the first channel 110 within the device layer 106. In the embodiment shown, the device layer 106 is a layer of either mono- or poly-crystalline silicon having a thickness of approximately 5 to 50 µm. The buried oxide layer 104 is shown having a thickness of approximately 0.5 to 2.5 µm FIG. 4 depicts the electronic device 200 of FIG. 3 with only the first metal portion 118 disposed above the passivation layer 116 and positioned proximate to the first channel 110. Similar to the electronic device 100 of FIG. 1, the first metal portion 118 can be configured as one or more of an upper electrode, a local heater element, and a Seebeck element.

Figure 5:
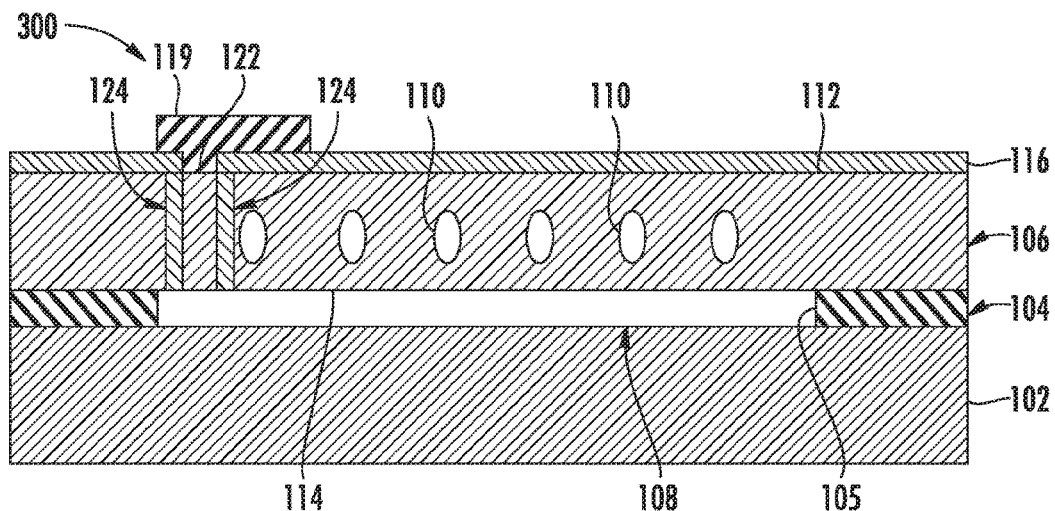
FIG. 5 depicts the electronic device of FIG. 3 with a side electrode positioned proximately lateral to a portion of the channel for electrostatically biasing the conveyed material.
Figure 6:
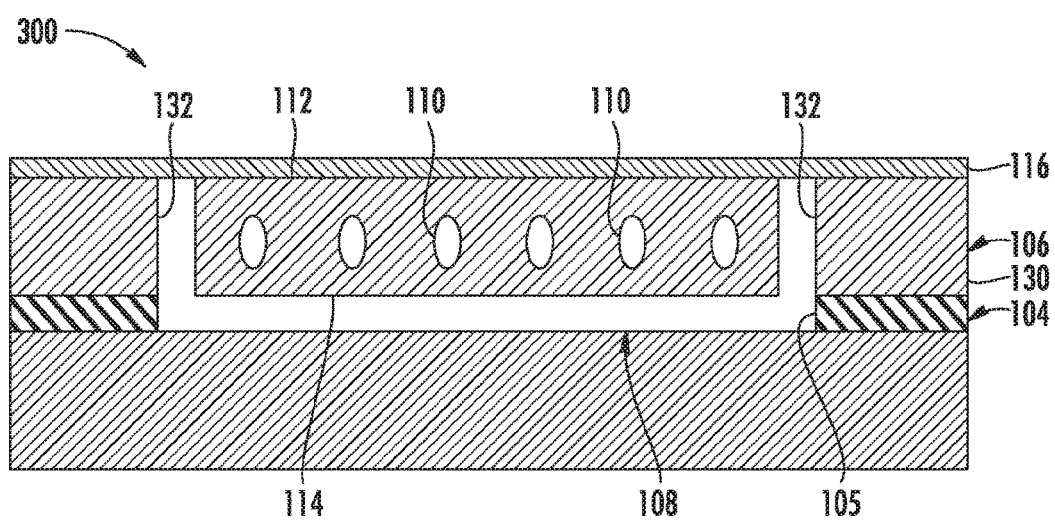
FIG. 6 depicts the electronic device of FIG. 3 having a trench portion substantially surrounding an inner portion of the device layer to thermally decouple the channel from an outer portion of the device layer.

FIG. 5 shows the electronic device 200 of FIG. 3 with only the side electrode 122 defined within the device layer 106. The side electrode 122 is positioned proximate to at least a portion of the channel 110 such that side electrode 122 can electrostatically bias the material passing through the portion of the channel 110 near the side electrode 122. FIG. 6 depicts the electronic device 200 of FIG. 3 with only the trench portion 132 disposed within the device layer 106 to thermally decouple the first portion 128 of the device layer 106 from the second portion 130.

Figure 7:
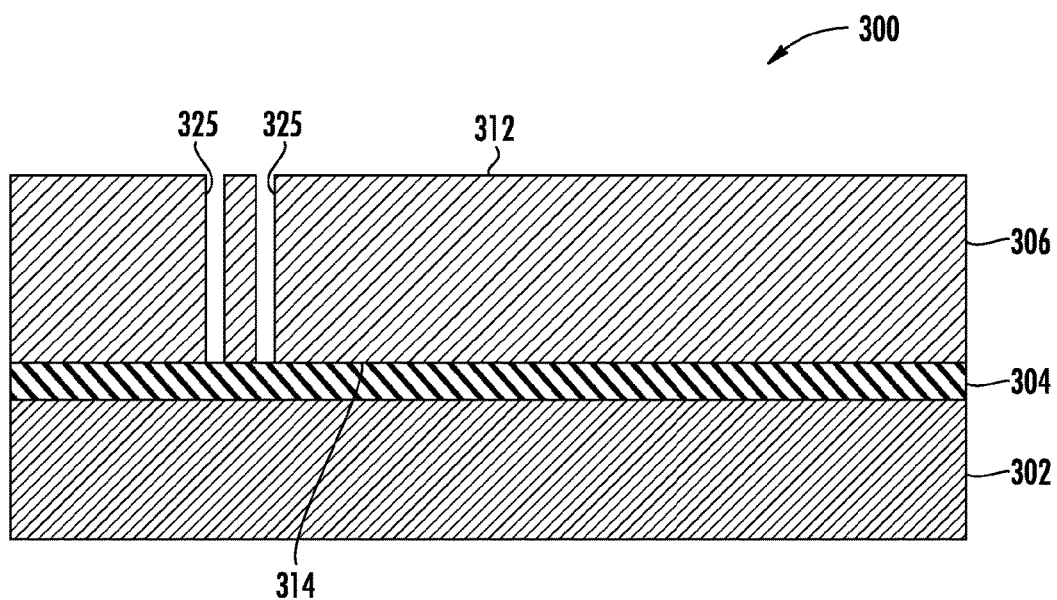
FIGS. 7-15 depict a process for forming the electronic device of FIG. 1.
Figure 8:
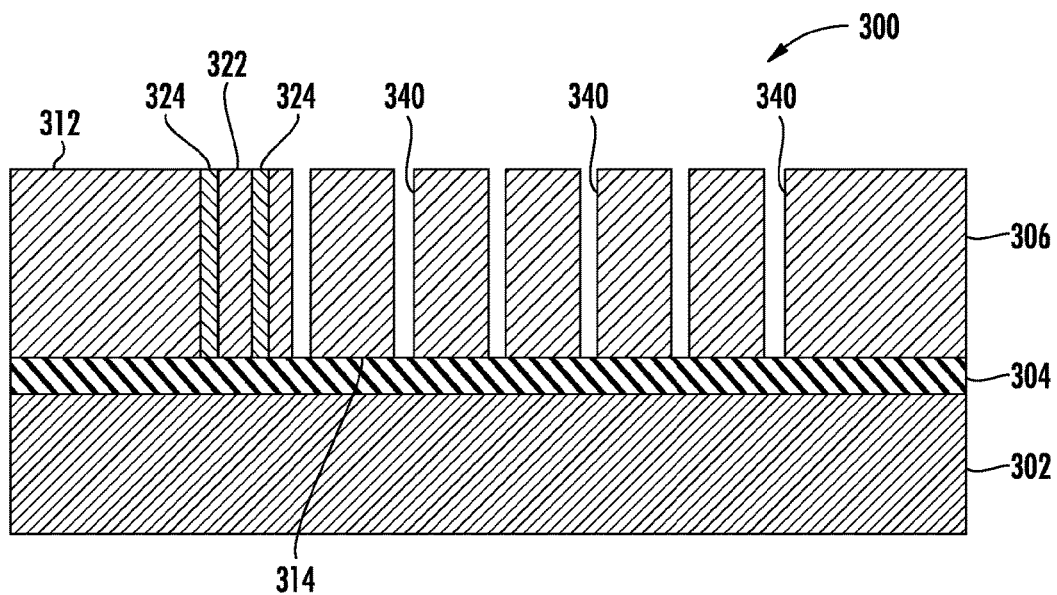

A process for forming an electronic device such as the electronic device 100 is discussed below with reference to FIGS. 7-16. Referring initially to FIG. 7, a silicon-on-insulator (SOI) wafer 300 including a base layer 302, a buried oxide layer 304, and a device layer 306 is initially etched to define a first trench portion 325 through the device layer 306 and between an upper surface 312 and a lower surface 314 of the device layer 306. Referring now to FIG. 8, the first trench portion 125 is filled with a low stress nitride to form a nitride portion or spacer 324 that defines an electrically isolated side electrode 322 within the device layer 306. After the spacer 324 is formed, the device layer 306 is etched again to define a plurality of channel-forming trenches 340 between the upper and the lower surfaces 312, 314 of the device layer 306.

Figure 9:
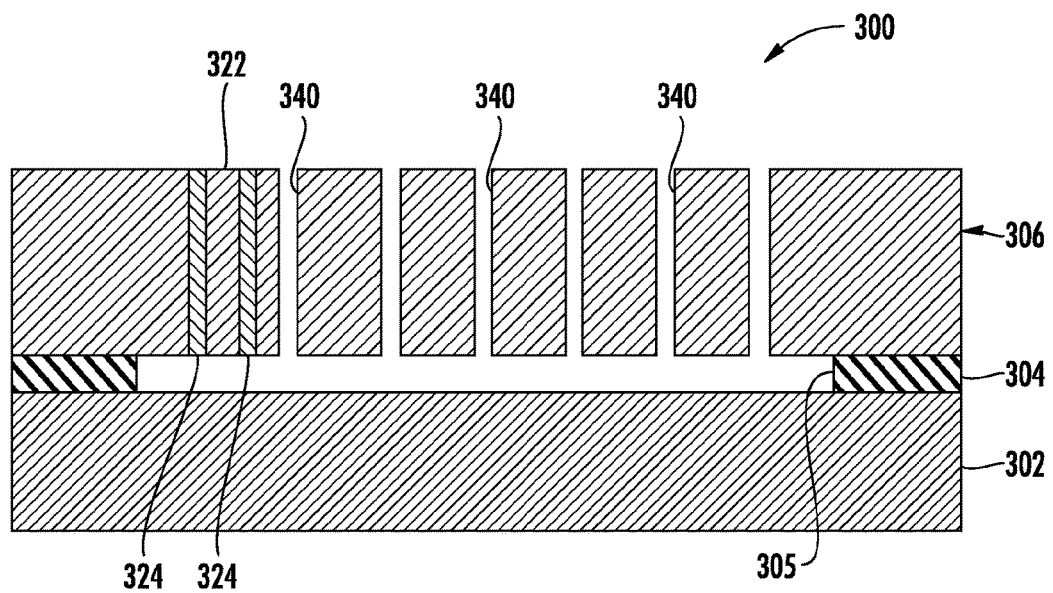
Figure 10:
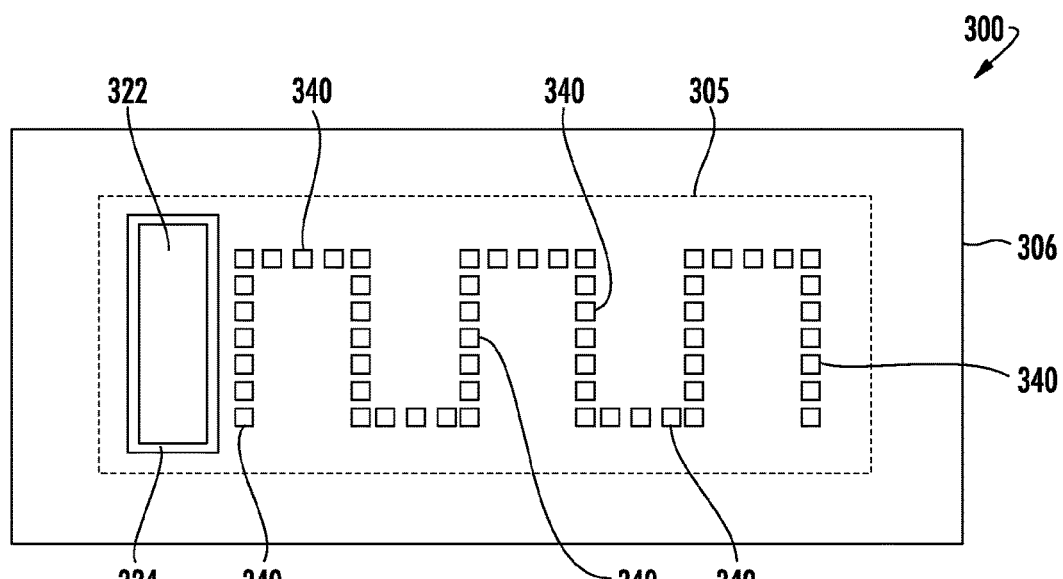

FIGS. 9 and 10 depict a section view and a top view, respectively, of the wafer 300 after a hydrofluoric acid (HF) vapor etch release is performed which releases a portion of the buried oxide layer 304 located proximate to the channel-forming trenches 340. A portion 305 of the buried oxide layer 304 not released by the HF vapor etch release remains to anchor the device layer 306 to the base layer 302.

With particular reference to FIG. 10, the spaced channel-forming trenches 340 in the embodiment shown are aligned one-behind-the-other along a path in the device layer 306 in the form of a repeating square wave. In other embodiments, the channel-forming trenches 340 may be aligned along channel paths of different forms such as a repeating sine wave, a triangular wave, a sawtooth wave, and/or a meandering path through the device layer 306.

In some embodiments, the device layer 306 is etched to define a single trench (not shown) that defines a continuous channel-forming trench that extends through the device layer 306. The continuous channel-forming trench in this embodiment follows a path substantially similar to that of the spaced channel-forming trenches 340 described above with reference to FIG. 10. In some embodiments, the device layer 306 of the wafer 300 may include one or more distinct channel-forming portions similar to the spaced channel-forming trenches 340 and the continuous channel-forming trench.

After one or more of the spaced channel-forming trenches 340 and the continuous channel-forming trench are formed in the device layer 306 (FIG. 10), the SOI wafer 300 is subjected to an annealing process in a reducing ambient. The reducing ambient in the embodiment shown is hydrogen ($H_2$) ambient, while other reducing ambients may be used in other embodiments. The annealing process is carried out at an elevated temperature greater than 1000 degrees Celsius for a duration of ten (10) seconds to ten (10) minutes.

Figure 11:
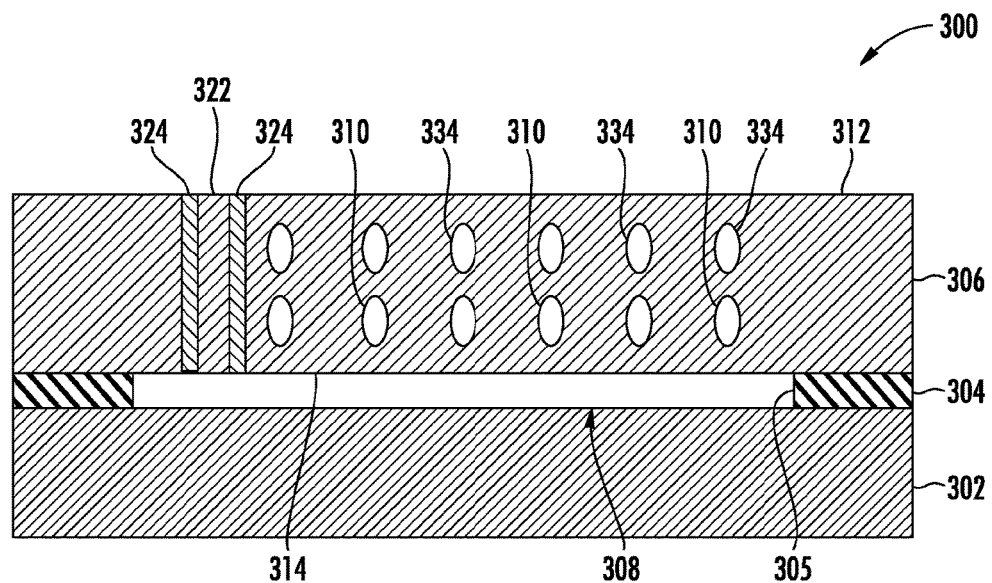
Figure 12:
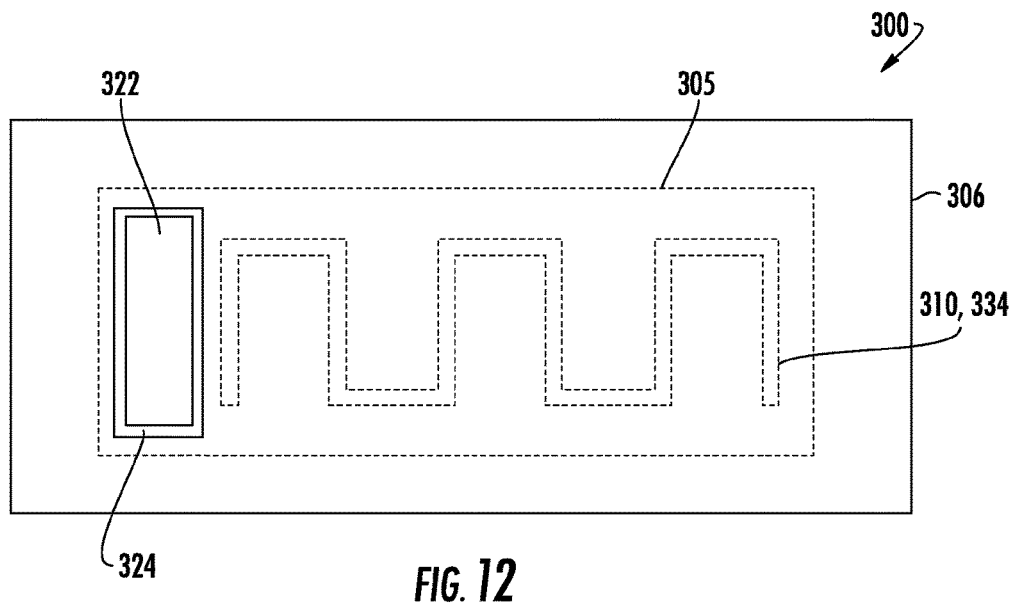

FIGS. 11 and 12 depict section and top views, respectively, of the SOI wafer 300 after the wafer 300 is subjected to the annealing process. As shown in the figures, the annealing of the wafer 300 enables portions of silicon in the device layer 306 to migrate across the channel-forming trenches 340 near the upper and the lower surfaces 312, 314 of the device layer 306 and seal off the trenches 340 at the upper and the lower surfaces 312, 314. The spacing of the channel-forming trenches 340 along the channel path in the device layer 306 is such that a portion of the silicon between adjacent channel-forming trenches migrates towards the upper and the lower surfaces 312, 314 and across the channel-forming trenches 340. As the silicon portions between the adjacent channel-forming trenches continue to migrate towards the upper and the lower surfaces 312, 314, the channel-forming trenches unite and form a smooth channel portion therebetween.

The continued migration of silicon portions across all of the channel-forming trenches and from between all adjacent channel-forming trenches results in the formation of one or more atomic-smooth, continuous channels through the device layer 306. In the embodiment shown in FIG. 11, the annealing process forms a continuous first channel 310 and a continuous second channel 324 similar to the first and the second channels 110, 134 discussed above with reference to FIGS. 1 and 2. The sealing off of the channel-forming trenches 340 at the lower surface 314 of the device layer due to the annealing process also defines a cavity 308 bounded by the base layer 302, the buried oxide layer 304, and the device layer 306. The process of silicon migration is described in more detail in U.S. Pat. No. 7,235,456, the disclosure of which is incorporated herein by reference in its entirety.

Figure 13:
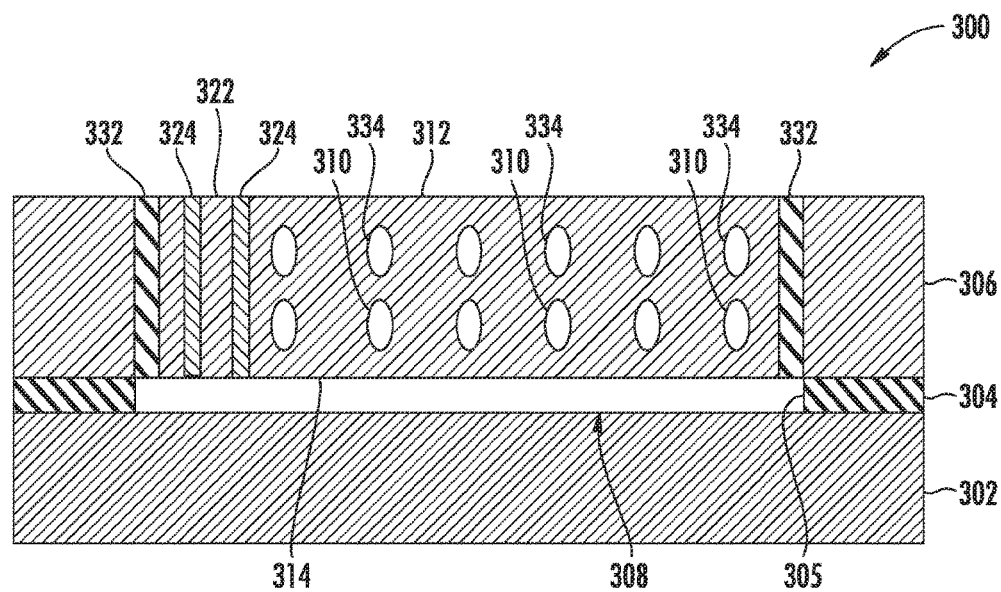
Figure 14:
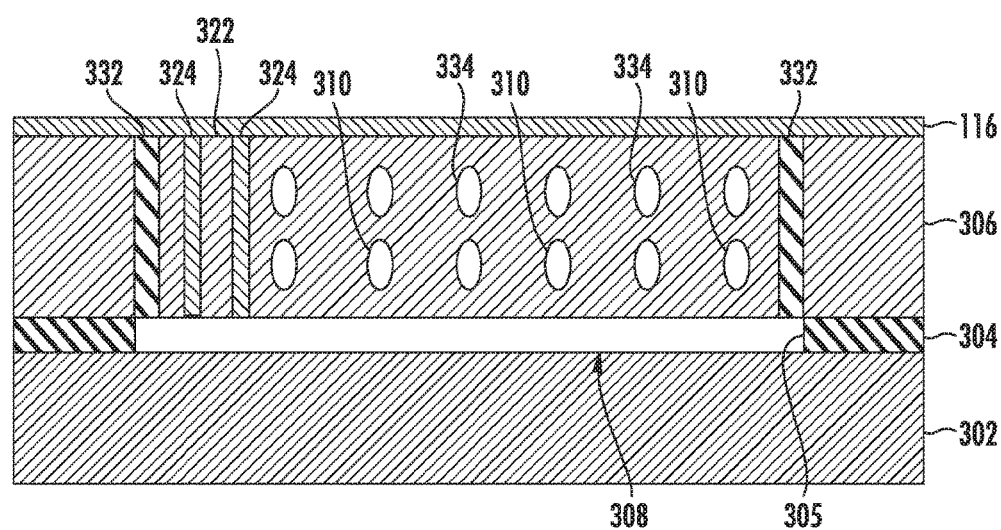
Figure 15:
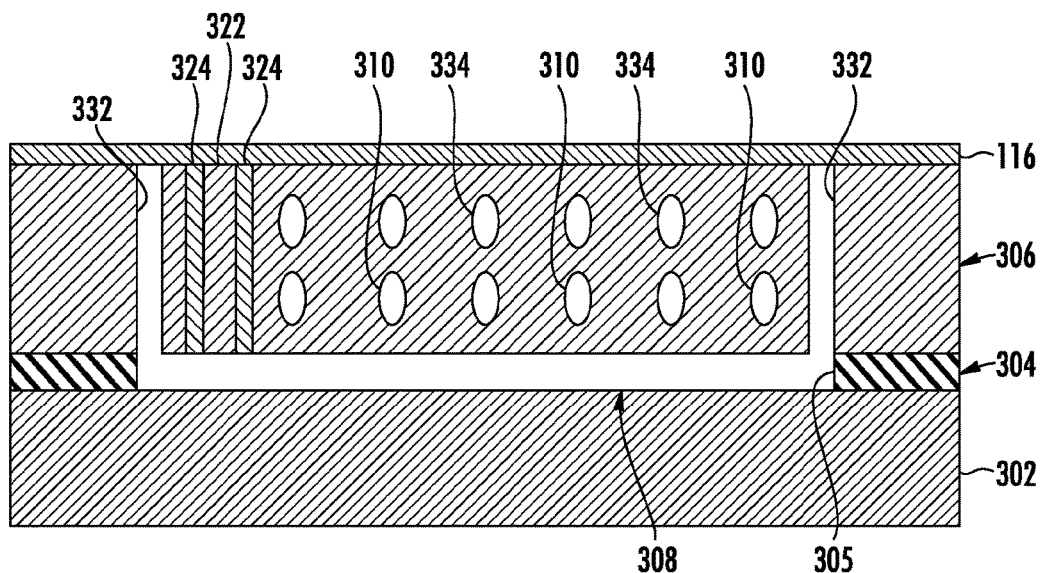

In the embodiment depicted in FIGS. 13-15, the device layer 306 includes a second trench portion 332 etched between the passivation layer 116 and the cavity 308. The second trench portion 332 is etched and refilled with oxide prior to the annealing of the SOI wafer 300 (FIG. 13). A passivation layer 116 is then deposited above the device layer 306, the spacer 324, and the oxide-filled second trench portion 332 (FIG. 14). A plurality of vent holes (not shown) is etched through the passivation layer 116 at locations corresponding to the oxide-filled second trench portion 332. An HF vapor etch release is performed which releases the oxide within the second trench portion 332 to isolate a first portion 328 of the device layer 306 from a second portion 330 (FIG. 15). A clean high temperature seal is then performed in an epi reactor to seal the vent holes.

The SOI wafer 300 provided according to the above-described process can be further processed to form the electronic device 100 of FIGS. 1 and 2. With continuing reference to FIGS. 1 and 2, a portion of the passivation layer 116 adjacent to the side electrode is patterned to expose the side electrode 122. A metal layer is then deposited above the passivation layer 116 and the exposed side electrode 122. The metal layer is patterned to form the first metal portion 118 above the channels 110, 134 and the second metal portion 119 which contacts the side electrode 122 through the patterned portion of the passivation layer 116 for electrical communication therebetween.

The process described above with reference to FIGS. 7-15 may be modified in a number of ways to provide additional electronic device variants such as those variants described above with reference to FIGS. 3-6. The electronic device 300 of FIG. 3 is provided by etching the channel-forming trenches (340 in FIG. 8) through a device layer having a relatively thin thickness (compare 106 in FIGS. 3 to 306 in FIG. 8). The thinner device layer 106 enables the channel-forming trenches to extend for a lesser length between the upper and the lower surfaces of the device layer 106. Accordingly, when the SOI wafer is annealed as described above with reference to FIGS. 11 and 12, the resulting silicon migration forms a single, atomic-smooth, continuous channel 110 within the device layer 106. A passivation layer 116 is then deposited over the sealed device layer 106.

FIG. 4 depicts the electronic device 300 of FIG. 3 with a first metal portion 118 patterned from a metal layer deposited above the passivation layer 116. FIG. 5 shows the electronic device 300 of FIG. 3 with a side electrode 122 defined within the device layer 106. Prior to forming the first channel 110, the device layer 106 is etched to form a trench portion (325 in FIG. 7). The trench portion 325 is then filled with a nitride portion to form a spacer 124, which electrically isolates the side electrode 122 therein. The passivation layer 116 is patterned to expose a portion of the side electrode 122. A metal layer is deposited above the passivation layer 116 and the exposed side electrode 122. The metal layer is then patterned to form a metal portion 119 in electrical communication with the side electrode 122. FIG. 6 shows the electronic device 300 of FIG. 3 with a second trench portion 132 etched through the device layer 106 in accordance with the process described with reference to FIGS. 13-14. The second trench portion 132 thermally decouples the first portion 128 of the device layer 106, which includes the first channel 110, from the second portion 130.

Figure 16:
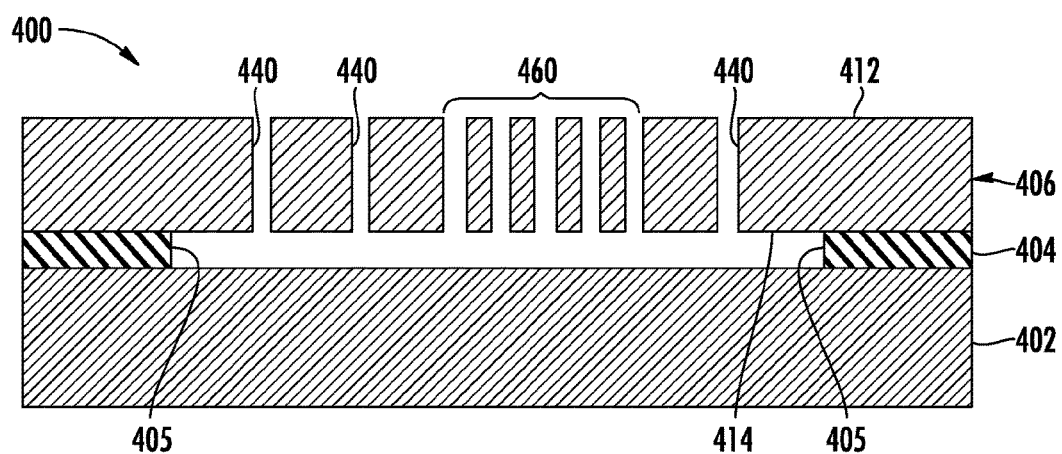
FIGS. 16 and 17 depict a process for forming an electronic device with a continuous channel having a varying cross section along a channel path through the electronic device.

FIGS. 16-19 illustrate a further modification of the above described process to form an electronic device with a continuous channel having different cross sections along the channel path. Referring initially to FIG. 16, an SOI wafer 400 including a base layer 402, a buried oxide layer 404, and a device layer 406 is etched in a similar manner as the SOI wafer 300 (FIGS. 9 and 10) to define a plurality of channel-forming trenches 440 through the device layer 406 and between an upper surface 412 and a lower surface 414 of the device layer 406. After the channel-forming trenches 440 are formed, a hydrofluoric acid (HF) vapor etch release is performed which releases a portion of the buried oxide layer 404 located proximate to the channel-forming trenches 440. The portion 405 of the buried oxide layer 404 not released by the HF vapor etch release remains to anchor the device layer 406 to the base layer 402.

Figure 17:
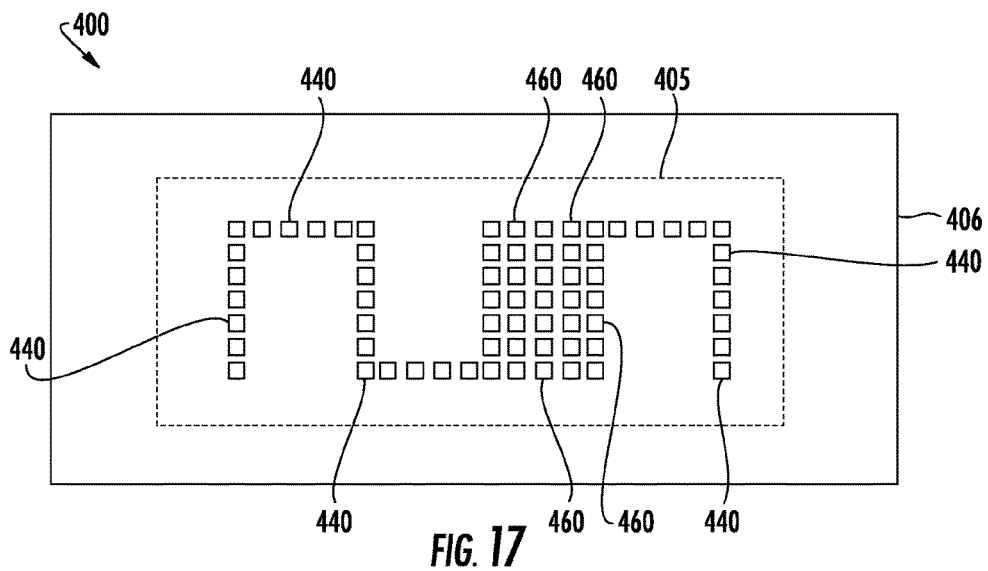

FIG. 17 shows a top view of the SOI wafer 400 of FIG. 16 after performance of the HF vapor etch release. The SOI wafer 400 in the embodiment shown in FIGS. 16 and 17 differs from the SOI wafer 300 shown in FIGS. 9 and 10 in that the wafer 400 includes at least one portion of trenches 460 arranged both one-behind-the-other and side-by-side along the channel path in the device layer 406. Although the transition from the trenches 440 to the trenches 460 is shown going from one-trench-wide to five-trenches-wide, other transition configurations are possible. For example, the number of side-by-side trenches for any portion of the channel path may increase or decrease by one or more trenches at every consecutive trench position along the channel path to form a graded transition.

Figure 18:
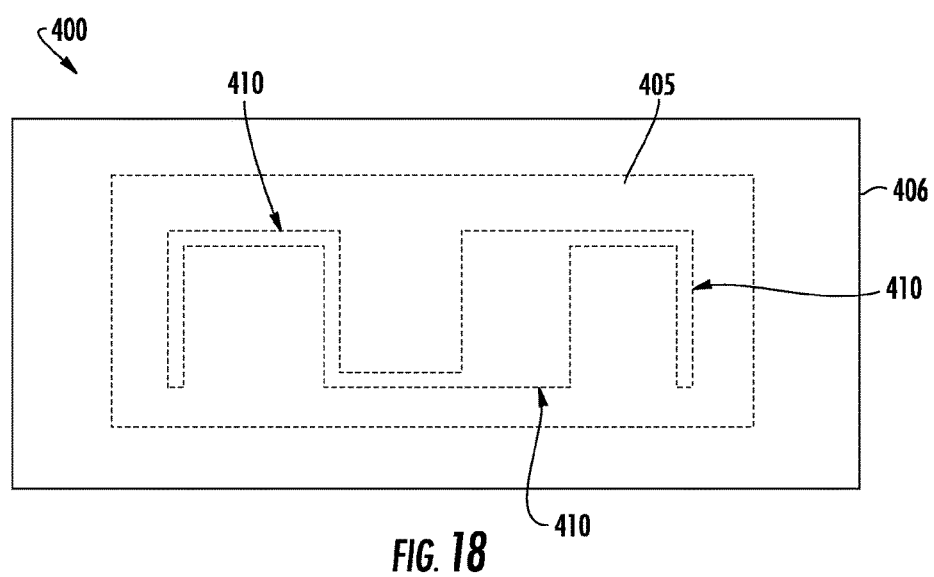
FIG. 18 shows a top view of the electronic device provided in accordance with the process of FIGS. 16 and 17.
Figure 19:
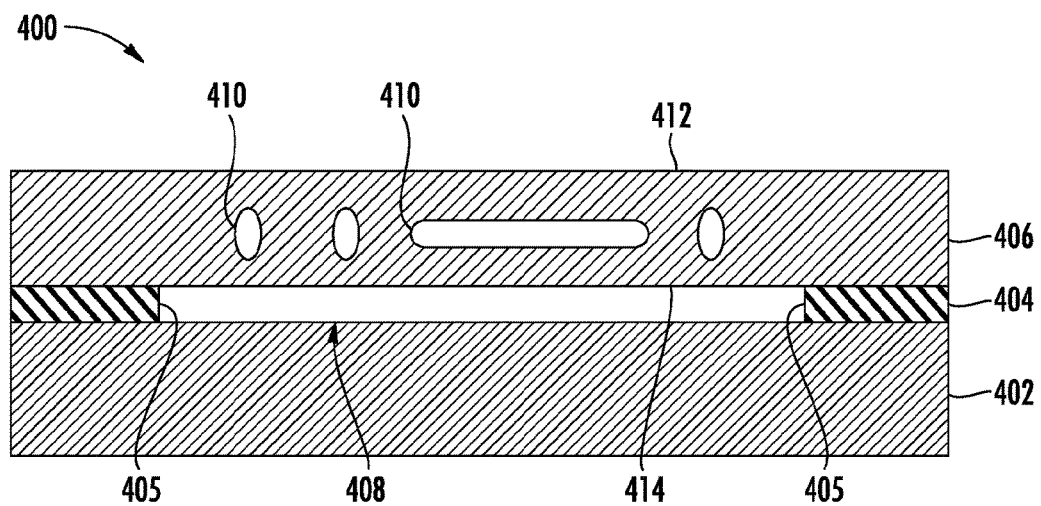
FIG. 19 shows a side cross-sectional view of the electronic device provided in accordance with the process of FIGS. 16 and 17.

FIGS. 18 and 19 show the SOI wafer 400 of FIGS. 16 and 17 after the wafer 400 is subjected to the annealing process as described above. The migration of silicon portions across all of the channel-forming trenches 440, 460 and from between all adjacent channel-forming trenches 440, 460 results in the formation of an atomic-smooth, continuous channel 410 through the device layer 406. The annealing process also results in the formation of a cavity 408 defined by the base layer 402, the device layer 406, and the remaining portions 405 of the buried oxide layer 404 after the annealing process. As shown in the figures, the annealing of SOI wafer 400 results in the channel 410 having a plate-like cross section along the portion of the channel formed from the trenches 460. Although a plate-like cross section is depicted in FIGS. 16 and 17, other cross sectional geometries may be formed by varying one or more of the number, the spacing, the geometry, and the path of the channel-forming trenches formed in the device layer.

The above-described processes enable the production of micro-gas-chromatographs with novel separator columns. The separator columns provided by the disclosed methods enable small channel cross sections and long channel lengths with atomic smooth channel sidewalls, high channel packaging density, multiple channels positioned on top of each other, and channel segments that are thermally decoupled from the substrates. Furthermore, the micro-gas-chromatographs produced according to the above-described processes enable electrostatic and thermal actuators to be positioned in close proximity to the separator columns such that the material passing through the columns can be locally heated and/or cooled and/or electrically biased.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method of forming a microelectromechanical system (MEMS) device, comprising:
   providing a silicon-on-insulator (SOI) wafer including a base layer, a device layer above the base layer, and a buried oxide layer between the base layer and a lower surface of the device layer;
   etching a plurality of trenches from an upper surface of the device layer to the buried oxide layer, the trenches spaced along a sequential path in the device layer;
   releasing a portion of the buried oxide layer through the trenches; and
   annealing the SOI wafer to seal off the trenches at the upper and lower surfaces of the device layer so as to form (i) one or more atomic-smooth, continuous channels within the device layer and (ii) a cavity bounded by the base layer, the buried oxide layer, and the lower surface of the device layer.

2. The method of claim 1, wherein:
   the one or more atomic-smooth, continuous channels includes a first continuous channel and a second continuous channel, and
   the device layer defines (i) a first ingress leading into the first continuous channel and a first egress leading out of first continuous channel and (ii) a second ingress leading into the second continuous channel and a second egress leading out of the second continuous channel.

3. The method of claim 2, wherein:
   the first continuous channel is disposed substantially along a first plane through the device layer,
   the second continuous channel is disposed substantially along a second plane through the device layer, the second plane spaced from the first plane, and
   the first egress of the first continuous channel is joined to the second ingress of the second continuous channel such that first and second continuous channels form a single continuous channel passing through the device layer.

4. The method of claim 1, further comprising:
   etching a trench portion from the upper surface of the device layer to the buried oxide layer, the trench portion encompassing a first portion of the device layer that includes the one or more atomic-smooth, continuous channels;
   filling the trench portion with an oxide;
   depositing a passivation layer above the device layer and the oxide-filled trench portion;
   etching a plurality of vent holes through the passivation layer at locations corresponding to the oxide-filled trench portion;
   releasing the oxide from within the trench portion to thermally decouple the first portion of the device layer from a second portion of the device layer; and
   sealing the vent holes.

5. The method of claim 4, wherein:
   releasing the oxide from within the trench portion includes performing a hydrofluoric acid (HF) vapor etch release, and
   sealing the vent holes includes performing a clean high temperature seal in an epi reactor.

6. The method of claim 1, further comprising:
   forming a spacer from the upper surface of the device layer to the buried oxide layer to electrically isolate a side electrode within the device layer prior to etching the plurality of trenches, the spacer positioned proximate to at least a portion of the one or more atomic-smooth continuous channels, depositing a passivation layer above the device layer, the spacer and the side electrode;

patterning a portion of the passivation layer to expose the side electrode;

depositing a metal layer above the patterned passivation layer and the exposed side electrode; and patterning the metal layer to form a metal portion that is in electrical communication with the side electrode, the metal portion and the side electrode enabling electrostatic biasing of a material conveyed through the one or more atomic-smooth, continuous channels.

7. The method of claim 1, further comprising:
depositing a passivation layer above the device layer;
depositing a metal layer above the passivation layer;
patterning the metal layer to form a metal portion proximate to a portion of the one or more atomic-smooth, continuous channels,
wherein the metal portion is configured as one more of an upper electrode, a local heater element, and a Seebeck element.

8. The method of claim 1, wherein the sequential path of the spaced trenches forms one or more of a repeating square wave, a repeating sine wave, a triangular wave, a sawtooth wave, and a meandering path through the device layer when viewed facing the upper surface of the device layer from above.

9. The method of claim 1, wherein the sequential path of spaced trenches includes trenches that are arranged in one or more of (i) a single-file line, one-trench-behind-the-other-trench and (ii) two or more trenches wide when viewed facing the upper surface of the device layer from above.

10. The method of claim 1, wherein the one or more atomic-smooth, continuous channels have cross sections that are one or more of constant, variable, and a combination of constant and variable portions when viewed along a section plane that passes perpendicular to a path of the channels through the device layer.

11. The method of claim 1, wherein annealing the SOI wafer comprises annealing the SOI wafer:
in a reducing ambient,
at an elevated temperature greater than 1000 degrees Celsius, and
for a duration of 10 seconds to 10 minutes.

12. The method of claim 1, wherein releasing a portion of the buried oxide layer comprises performing a hydrofluoric acid (HF) vapor etch release.

13. The method of claim 1, wherein providing an SOI wafer comprises one of:
providing an SOI wafer having a device layer with a relatively thick layer thickness such that subsequent annealing of the SOI wafer forms at least two atomic-smooth, continuous channels within the device layer, or
providing an SOI wafer having a device layer with a relatively thin layer thickness such that subsequent annealing of the SOI wafer forms one atomic-smooth, continuous channel within the device layer.

14. A microelectromechanical system (MEMS) device, comprising:
a base layer;
a device layer supported vertically above the base layer by a portion of a buried oxide layer;
a cavity within the buried oxide layer and extending horizontally between the base layer and a released portion of the device layer; and
a passivation layer supporting the released portion of the device layer above the cavity, wherein the released portion includes at least one channel extending horizontally within the released portion beneath an upper surface of the released portion and a above lower surface of the released portion.

15. The MEMS device of claim 14, further comprising:
a side electrode defined within the released portion of the device layer by a spacer comprising a nitride portion, the side electrode positioned proximate to a portion of the at least one channel; and
a metal portion extending through a portion of the passivation layer such that the metal portion is in electrical communication with the side electrode.

16. The MEMS device of claim 14, further comprising:
a trench portion extending between the passivation layer and the cavity, the trench portion encompassing the released portion of the device layer such that the trench portion and the cavity thermally decouple the released portion from an unreleased portion of the device layer.

17. The MEMS device of claim 14, wherein:
the at least one channel includes a first channel and a second channel, and
the released portion of the device layer defines (i) a first ingress leading into the first channel and a first egress leading out of first channel and (ii) a second ingress leading into the second channel and a second egress leading out of the second channel.

18. The MEMS device of claim 17, wherein:
the first channel is disposed substantially along a first plane through the released portion of the device layer, and
the second channel is disposed substantially along a second plane through the released portion of the device layer, the second plane spaced from the first plane.

19. The MEMS device of claim 17, wherein the first and second channels are disposed substantially along a common plane through the released portion of the device layer.

20. The MEMS device of claim 14, wherein:
the device layer is a layer of either mono- or poly-crystalline silicon having a thickness of approximately 5 to 50 µm, and
the buried oxide layer has a thickness of approximately 0.5 to 2.5 µm.

* * * * *